United States Patent
Evans et al.

(10) Patent No.: US 11,471,627 B2
(45) Date of Patent: Oct. 18, 2022

(54) FLOW THERAPY SYSTEM AND METHOD

(71) Applicant: Fisher & Paykel Healthcare Limited, Auckland (NZ)

(72) Inventors: Alicia Jerram Hunter Evans, Auckland (NZ); Samantha Dale Oldfield, Auckland (NZ); Michael Robert Barraclough, Auckland (NZ); Dexter Chi Lun Cheung, Auckland (NZ); Callum James Thomas Spence, Auckland (NZ); Milanjot Singh Assi, Auckland (NZ); Hamish Adrian Osborne, Auckland (NZ); Thomas Heinrich Barnes, Surrey (GB); Matthew Jon Payton, Auckland (NZ); Craig Karl White, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 453 days.

(21) Appl. No.: 16/500,329

(22) PCT Filed: Apr. 5, 2018

(86) PCT No.: PCT/IB2018/052387
§ 371 (c)(1),
(2) Date: Oct. 2, 2019

(87) PCT Pub. No.: WO2018/185714
PCT Pub. Date: Oct. 11, 2018

(65) Prior Publication Data
US 2021/0138172 A1    May 13, 2021

Related U.S. Application Data

(60) Provisional application No. 62/481,804, filed on Apr. 5, 2017.

(51) Int. Cl.
*A61M 16/00* (2006.01)
*A61M 16/06* (2006.01)

(52) U.S. Cl.
CPC ...... *A61M 16/026* (2017.08); *A61M 16/0003* (2014.02); *A61M 16/0677* (2014.02);
(Continued)

(58) Field of Classification Search
CPC .......... A61M 16/026; A61M 2230/202; A61M 16/205; A61M 16/12; A61M 16/01; A61B 5/0826; A61B 5/14542
See application file for complete search history.

(56) References Cited

U.S. PATENT DOCUMENTS

| 6,223,064 B1 | 4/2001 | Lynn et al. |
| 7,201,734 B2 | 4/2007 | Hickle |

(Continued)

FOREIGN PATENT DOCUMENTS

| WO | WO 1994/004071 | 3/1994 |
| WO | WO 2010/053845 | 5/2010 |

(Continued)

OTHER PUBLICATIONS

Farmer et al. "A model to describe the rate of oxyhaemoglobin desaturation during apnea", 1996, British Journal of Anaesthesia, 76: 284-291 (Year: 1996).*
(Continued)

*Primary Examiner* — Margaret M Luarca
(74) *Attorney, Agent, or Firm* — Knobbe Martens Olson & Bear LLP

(57) ABSTRACT

A method of determining a duration of safe apnoea. Information is obtained relating to a respiratory indicator, and a duration of safe apnoea is determined from the obtained information. A respiratory therapy system has one or more patient interfaces. A processor is configured to determine a (Continued)

duration of safe apnoea based on obtained information relating to a respiratory indicator.

20 Claims, 11 Drawing Sheets

(52) U.S. Cl.
CPC ... *A61M 2230/04* (2013.01); *A61M 2230/202* (2013.01); *A61M 2230/205* (2013.01); *A61M 2230/42* (2013.01); *A61M 2230/46* (2013.01)

(56) References Cited

U.S. PATENT DOCUMENTS

| | | | |
|---|---|---|---|
| 8,028,694 | B2 | 10/2011 | Hickle |
| 8,670,811 | B2 | 3/2014 | O-Reilly |
| 9,636,056 | B2 | 5/2017 | Al-Ali |
| RE47,353 | E | 4/2019 | Kiani |
| 10,588,518 | B2 | 3/2020 | Kiani |
| 10,918,341 | B2 | 2/2021 | Al-Ali |
| 10,973,466 | B2 | 4/2021 | Payton et al. |
| 10,987,066 | B2 | 4/2021 | Chandran |
| 2009/0299430 | A1 | 12/2009 | Davies et al. |
| 2011/0006901 | A1 | 1/2011 | Cassidy |
| 2011/0067697 | A1 | 3/2011 | Lellouche et al. |
| 2013/0201020 | A1 | 8/2013 | Covidien |
| 2013/0253359 | A1 | 9/2013 | Emtell et al. |
| 2015/0258290 | A1* | 9/2015 | Landwehr ............... G16Z 99/00 128/202.22 |
| 2018/0085544 | A1 | 3/2018 | Holyoake et al. |
| 2018/0280641 | A1 | 10/2018 | White et al. |
| 2018/0311454 | A1 | 11/2018 | Klein et al. |
| 2020/0261675 | A1* | 8/2020 | Rehman ............... G16H 40/63 |
| 2021/0022676 | A1 | 1/2021 | Lamego et al. |
| 2021/0244365 | A1 | 8/2021 | Assouad |

FOREIGN PATENT DOCUMENTS

| | | |
|---|---|---|
| WO | WO 2013/158791 | 10/2013 |
| WO | WO 2016/133406 | 8/2016 |
| WO | WO 2016/157106 | 10/2016 |
| WO | WO 2018/136821 | 7/2018 |
| WO | WO 2018/185714 | 10/2018 |
| WO | WO 2019/070136 | 4/2019 |
| WO | WO 2019/089655 | 5/2019 |
| WO | WO 2021/202465 | 10/2021 |

OTHER PUBLICATIONS

Benumof, J.L. et al., "Critical hemoglobin desaturation will occur before return to an unparalyzed state following 1 mg/kg intravenous succinylcholine", Anesthesiology: The Journal of the American Society of Anesthesiologists, 1997, vol. 87, No. 4, pp. 979-982.

Biffen, A. et al., "Apnoea and Pre-Oxygenation Anaesthesia Tutorial of the Week", 2013, pp. 1-7. p. 2 line 1-5, p. 2 line 13-16, and p. 3 line 1-26.

Bouroche, G. and Bourgain, J.L., "Preoxygenation and general anesthesia: a review", Minerva Anestesiologica, 2015, vol. 81, No. 8, pp. 910-920. Figure 1; abstract; and p. 911 col. 2 line 33-40.

PCT International Search Report, Application No. PCT/IB2018/052387, dated Jun. 13, 2018, in 7 pages.

European Patent office, Supplementary European Search Report, Application No. EP 18781284, dated Nov. 20, 2020, in 1 page.

Farmery, A.D. and Roe, P.G., "A model to describe the rate of oxyhaemoglobin desaturation during apnoea", British Journal of Anaesthesia, 1996, vol. 76, No. 2, pp. 284-291.

Rajan, S. et al., "Effects of Preoxygenation with Tidal Volume Breathing Followed by Apneic Oxygenation with and without Continuous Positive Airway Pressure on Duration of Safe Apnea Time and Arterial Blood Gases", Anesthesia: Essays and Researches, 2018, vol. 12, No. I, pp. 229-233. Abstract; p. 232 col. 2 line 38-39.

Scott A. Sands et al: "A Model Analysis of Arterial Oxygen Desaturation during Apnea in Preterm Infants", PLOS Computational Biology, vol. 5, No. 12, Dec. 4, 2009 (Dec. 4, 2009), p. e1000588, XPO55752758.

* cited by examiner

FLOW THERAPY SYSTEM AND METHOD

TECHNICAL FIELD

The present disclosure generally relates to respiratory gas therapy. More particularly, the present disclosure relates to respiratory gas therapy systems, apparatus, and methods for treating patients receiving anaesthesia or undergoing intubation or endoscopy.

BACKGROUND ART

Intubation is often practiced on patients suffering from various illnesses or injuries. In general, patients who are sedated for a medical procedure require intubation as they often stop spontaneous breathing. In some cases, intubation of a patient can be completed in thirty to sixty seconds, but in other cases, particularly if the patient's airway is difficult to traverse (for example, due to cancer or severe injury), intubation can take much longer. To prevent hypoxia or hypoxemia during intubation, a medical professional performing the intubation will often pre-oxygenate the patient to be intubated by applying a face mask and delivering oxygen for a period of time until the patient's blood oxygen saturation level (measured using, for example, near infrared spectroscopy or pulse oximetry) reaches approximately 100%. Pre-oxygenation also denitrogenises the patient's lungs, creating an alveolar oxygen reservoir that serves to maintain oxygen saturation levels for a small post-ventilatory window. Pre-oxygenation can provide a buffer against undesirable declines in oxygen saturation, but for long intubation procedures, it is often necessary to interrupt the intubation process and reapply the face mask to again increase the patient's oxygen saturation level to adequate levels. The interruption of the intubation process, which can happen several times for a difficult intubation process, can be frustrating to the medical professional. Additionally, the patient can experience rises in blood carbon dioxide due to the poor management of physiological dead space. Similar difficulties can be encountered with patients undergoing, for example, upper endoscopies.

An apnoea is the temporary absence of breathing. It commonly occurs at the induction of anaesthesia. The duration of safe apnoea is defined as the time until a patient reaches a specified oxygen saturation level. Typically, that oxygen saturation level may be 88-90%, although that level may vary depending on the patient and procedure being carried out. Saturations below this level can rapidly deteriorate to critical levels (<70%) on the steep section of the oxyhaemoglobin dissociation curve posing significant risk to the patient. Alternatively, the duration of safe apnoea is defined as the time until a patient reaches a specified $CO_2$ saturation level. The duration of safe apnoea varies considerably and there are currently no methods to assess the duration of apnoea.

SUMMARY OF THE INVENTION

Thus, in accordance with certain features, aspects and advantages of at least one of the embodiments disclosed herein, a method of predicting a duration of safe apnoea is disclosed, the method comprising:
 measuring an indicator; and
 determining a duration of safe apnoea from the measured indicator.

In some configurations, the indicator is one or more of a respiratory indicator, and/or a physiological indicator.

In some configurations, the indicator (such as a respiratory indicator and/or a physiological indicator) comprises, or is based on, carbon dioxide concentration, carbon dioxide clearance, respiratory rate, oxygen concentration, arterial oxygen content, arterial carbon dioxide content, lung volume, lung compliance, lung/airway pressure, airway resistance/patency, V/Q mismatch (ventilation (V)-perfusion (Q)), heart rate, blood pressure, or metabolic rate.

In some configurations, the method comprises measuring a plurality of indicators (such as a respiratory indicator and/or a physiological indicator) of the patient comprising, or based on, two or more of carbon dioxide concentration or clearance, heart rate, respiratory rate, oxygen concentration, blood pressure, arterial oxygen or carbon dioxide content, lung volume, lung compliance, lung/airway pressure, airway resistance/patency, metabolic rate, V/Q mismatch (ventilation (V)-perfusion (Q)) heart rate, blood pressure, or metabolic rate.

In some configurations, the method comprises determining an average duration of safe apnoea from the plurality of measured indicators (such as a respiratory indicator and/or a physiological indicator). In some alternative configurations, the method comprises determining a plurality of durations of safe apnoea from the plurality of measured indicators (such as a respiratory indicator and/or a physiological indicator) and optionally further selecting the shortest duration of safe apnoea from the plurality of durations of safe apnoea In some configurations, the step of determining a duration of safe apnoea comprises comparing or fitting a model to the measured indicator (such as a respiratory indicator and/or a physiological indicator) to determine the duration of safe apnoea.

In some configurations, the method comprises measuring carbon dioxide as an indicator (such as a respiratory indicator and/or a physiological indicator), wherein the carbon dioxide is measured based on expired carbon dioxide, transcutaneous carbon dioxide, or blood gases. In some configurations, the step of determining a duration of safe apnoea comprises comparing the measured carbon dioxide to a maximum carbon dioxide limit. In some configurations, the maximum carbon dioxide limit is determined from a look up table with different carbon dioxide limits. In some configurations, the look up table comprises different carbon dioxide limits depending on one or more of disease, age, height, weight, pregnancy status, difficult airway type. In some alternative configurations, the maximum carbon dioxide limit is predetermined by a breath hold test to establish the maximum carbon dioxide level before the patient needs to breathe again.

In some configurations, the method comprises measuring oxygen concentration as an indicator (such as a respiratory indicator and/or a physiological indicator). In some configurations, the oxygen concentration is measured based on expired oxygen, transcutaneous oxygen, blood gases, haemoglobin oxygen concentration, blood pressure, arterial partial pressure of oxygen or arterial oxygen content.

In some configurations, the duration of safe apnoea is determined based on a threshold arterial partial pressure of oxygen (PaO2).

In some configurations, the threshold arterial oxygen content is determined from a threshold haemoglobin oxygen saturation (SpO2).

In some configurations, a user may input the specified threshold haemoglobin oxygen saturation ($SpO_2$) or threshold arterial partial pressure of oxygen (PaO2).

In some configurations, the threshold haemoglobin oxygen saturation ($SpO_2$), or threshold arterial partial pressure of oxygen (PaO2) may be a predetermined value.

In some configurations, the duration of safe apnoea is based on, or for example may be equal to, a length of time until the arterial partial pressure of oxygen reaches the threshold arterial partial pressure of oxygen In some configurations, the length of time until the arterial partial pressure of oxygen reaches the threshold arterial partial pressure of oxygen is determined by measuring or estimating a rate of change of arterial partial pressure of oxygen.

Additionally, in accordance with certain features, aspects and advantages of at least one of the embodiments disclosed herein, a respiratory therapy system is disclosed, the system comprising:

one or more patient interfaces; and a processor configured to determine a duration of safe apnoea from a measured indicator.

In some configurations, the indicator is one or more of a respiratory indicator, and/or a physiological indicator.

In some configurations, the processor is a remote processor.

In some configurations, the respiratory indicator (such as a respiratory indicator and/or a physiological indicator) comprises, or is based on, carbon dioxide concentration, carbon dioxide clearance, respiratory rate, oxygen concentration, arterial oxygen, arterial carbon dioxide content, lung volume, lung compliance, lung/airway pressure, airway resistance/patency, V/Q mismatch (ventilation (V)-perfusion (Q)), heart rate, blood pressure, or metabolic rate.

In some configurations, the processor is configured to determine the duration of safe apnoea from a plurality of indicators(such as a respiratory indicator and/or a physiological indicator) comprising, or based on, two or more of carbon dioxide concentration, carbon dioxide clearance, respiratory rate, oxygen concentration, arterial oxygen, arterial carbon dioxide content, lung volume, lung compliance, lung/airway pressure, airway resistance/patency, V/Q mismatch (ventilation (V)-perfusion (Q)), heart rate, blood pressure, or metabolic rate.

In some configurations, the processor is configured to determine an average duration of safe apnoea from the plurality of measured indicators (such as a respiratory indicator and/or a physiological indicator). In some alternative configurations, the processor is configured to determine a plurality of durations of safe apnoea from the plurality of measured indicators (such as a respiratory indicator and/or a physiological indicator) and further optionally wherein the processor selects the shortest duration of safe apnoea from the plurality of durations of safe apnoea.

In some configurations, the processor is configured to compare or fit a model to the measured indicator (such as a respiratory indicator and/or a physiological indicator) determine the duration of safe apnoea.

In some configurations, the or an indicator (such as a respiratory indicator and/or a physiological indicator) comprises measured carbon dioxide, and the processor is configured to compare the measured carbon dioxide to a maximum carbon dioxide limit to determine the duration of safe apnoea. In some configurations, the processor is configured to determine the maximum carbon dioxide limit from a look up table with different carbon dioxide limits. In some configurations, the look up table comprises different carbon dioxide limits depending on one or more or a combination of disease, age, height, weight, pregnancy status, difficult airway type. In some configurations, the processor is configured to compare the measured carbon dioxide to a predetermined maximum carbon dioxide limit to predict the duration of safe apnoea.

In some configurations, the system is configured to measure oxygen concentration as an indicator.

In some configurations, the oxygen concentration is measured based on expired oxygen, transcutaneous oxygen, blood gases, haemoglobin oxygen concentration, blood pressure, arterial partial pressure of oxygen, or arterial oxygen content.

In some configurations, the processor is configured to determine the duration of safe apnoea based on a threshold arterial partial pressure of oxygen (PaO2).

In some configurations, the threshold arterial oxygen content is determined from a threshold haemoglobin oxygen saturation (SpO2).

In some configurations, the system may comprise comprising a user interface to enable a user to input the threshold haemoglobin oxygen saturation ($SpO_2$), or threshold arterial partial pressure of oxygen (PaO2).

In some configurations, the threshold haemoglobin oxygen saturation ($SpO_2$), or threshold arterial partial pressure of oxygen (PaO2) may be a predetermined value.

In some configurations, the processor is configured to determine the duration of safe apnoea based on, a length of time until the arterial partial pressure of oxygen reaches the threshold arterial partial pressure of oxygen In some configurations, the length of time until the arterial partial pressure of oxygen reaches the threshold arterial partial pressure of oxygen is determined by the processor by measuring or estimating a rate of change of arterial partial pressure of oxygen.

Additionally, in accordance with certain features, aspects and advantages of at least one of the embodiments disclosed herein, a method of determining a duration of safe apnoea is disclosed, the method comprising:

determining a duration of safe apnoea based on a relationship between haemoglobin oxygen saturation (SpO2) and arterial partial pressure of oxygen (PaO2).

In some configurations, the method comprises measuring SpO2 and PaO2 at set times. In some configurations, the measuring of SpO2 comprises using pulse oximetry.

In some configurations, the measuring of PaO2 comprises measuring blood gases or inferring the PaO2 from a transcutaneous oxygen measurement.

In some configurations, the method comprises determining a PaO2 value that relates to a specified minimum safe value of SpO2. In some configurations, the specified minimum safe value of SpO2 is a predetermined value or is a user input value. In some configurations, the minimum safe value of SpO2 is about 90%.

In some configurations, the method comprises determining the time remaining until the determined PaO2 value is reached, based on a relationship between measured PaO2 values and time.

In some configurations, the method comprises determining the time remaining until the determined PaO2 value is reached, based on a rate of change of PaO2.

Additionally, in accordance with certain features, aspects and advantages of at least one of the embodiments disclosed herein, a respiratory therapy system is disclosed, the system comprising:

one or more patient interfaces; and a processor configured to determine a duration of safe apnoea based on a relationship between haemoglobin oxygen saturation (SpO2) and arterial partial pressure of oxygen (PaO2).

In some configurations, the processor is a remote processor.

In some configurations, the system is configured to predict the duration of safe apnoea based on a relationship between measured values of SpO2 and PaO2 at set times. In some configurations, the processor is configured to determine a PaO2 value that relates to a specified minimum safe value of SpO2. In some configurations, the specified minimum safe value of SpO2 is a predetermined value. In some alternative configurations, the system comprises a user interface to enable a user to input the specified minimum safe value of SpO2.

In some configurations, the processor is configured to determine the time remaining until the determined PaO2 value is reached, based on a relationship between measured PaO2 values and time.

In some configurations, the method comprises determining the time remaining until the determined PaO2 value is reached, based on a rate of change of PaO2.

Additionally, in accordance with certain features, aspects and advantages of at least one of the embodiments disclosed herein, a respiratory therapy system is disclosed, the system comprising a method of determining a duration of safe apnoea, the method comprising:

determining a duration of safe apnoea based on a relationship between a patient's oxygen reservoir and the patient's oxygen consumption.

In some configurations, the method comprises determining the functional residual capacity of a patient's lungs to estimate a maximum oxygen reservoir volume. In some configurations, the step of determining the functional residual capacity comprises estimating the functional residual capacity using one or more of nitrogen washout, helium dilution, body plethysmography, using a look up table.

In some configurations, the method comprises measuring or predicting a fraction of expired oxygen in the patient's lungs. In some configurations, the method comprises determining the patient's oxygen reservoir based on the maximum oxygen reservoir volume less the amount or volume or fraction of expired oxygen, plus an amount or volume of oxygen provided to the patient by the respiratory therapy system, if any. In some configurations, the method comprises determining the patient's oxygen consumption by estimating the patient's oxygen consumption based on weight, or metabolic rate, or measuring or estimating the patient's oxygen consumption, or measuring or estimating a $CO_2$ volume or concentration at or near a patient's airway.

In some configurations, the method comprises determining the duration of safe apnoea based on the patient's determined oxygen reservoir divided by the patient's oxygen consumption.

Additionally, in accordance with certain features, aspects and advantages of at least one of the embodiments disclosed herein, a respiratory therapy system is disclosed, the system comprising:

one or more patient interfaces; and a processor configured to determine a duration of safe apnoea based on a relationship between a patient's oxygen reservoir and the patient's oxygen consumption.

In some configurations, the processor is a remote processor.

In some configurations, the processor is configured to determine the patient's oxygen reservoir based on a maximum oxygen reservoir volume, less an amount or volume or fraction of expired oxygen, plus an amount or volume of oxygen provided by the respiratory therapy system, if any. In some configurations, the processor is configured to determine the duration of safe apnoea based on the patient's determined oxygen reservoir divided by the patient's oxygen consumption.

In some configurations, the system may be configured to determine the patient's oxygen consumption by estimating the patient's oxygen consumption based on weight, or metabolic rate, or measuring or estimating the patient's oxygen consumption, or measuring or estimating a $CO_2$ volume or concentration at or near a patient's airway.

Additionally, in accordance with certain features, aspects and advantages of at least one of the embodiments disclosed herein, a method of determining a duration of safe apnoea is disclosed, the method comprising:

determining a duration of safe apnoea based on one or more parameters relating to pre-oxygenation of a patient.

In some configurations, the parameter(s) is/are indicative of the effort to pre-oxygenate the patient.

In some configurations, the parameters comprise one or more of: a relationship of fraction of oxygen in expired air and fraction of inspired oxygen, a relationship of haemoglobin oxygen saturation and fraction of inspired oxygen, a relationship of arterial partial pressure of oxygen and fraction of inspired oxygen, the time to pre-oxygenate, the patient's metabolic rate.

In some configurations, the method comprises using one or more mathematical formulae or relationships to determine the duration of safe apnoea based on the one or more parameters.

Additionally, in accordance with certain features, aspects and advantages of at least one of the embodiments disclosed herein, a respiratory therapy system is disclosed, the system comprising:

one or more patient interfaces; and a processor configured to determine a duration of safe apnoea based on one or more parameters relating to pre-oxygenation of a patient.

In some configurations, the processor is a remote processor.

In some configurations, the parameter(s) is/are indicative of the effort to pre-oxygenate the patient.

In some configurations, the processor is configured to determine the duration of safe apnoea based on one or more of: a relationship of fraction of oxygen in expired air and fraction of inspired oxygen, a relationship of haemoglobin oxygen saturation and fraction of inspired oxygen, a relationship of arterial partial pressure of oxygen and fraction of inspired oxygen, the time to pre-oxygenate, the patient's metabolic rate.

In some configurations, the processor is configured to determine the duration of safe apnoea based on the one or more parameters using one or more mathematical formulae or relationships.

Additionally, in accordance with certain features, aspects and advantages of at least one of the embodiments disclosed herein, a method of determining a duration of safe apnoea is disclosed, the method comprising:

obtaining information relating to an indicator; and determining a duration of safe apnoea from the obtained information.

In some configurations, the indicator is one or more of a respiratory indicator, and/or a physiological indicator.

In some configurations, the method may have any one or more of the features disclosed herein.

Additionally, in accordance with certain features, aspects and advantages of at least one of the embodiments disclosed herein, a respiratory therapy system is disclosed, the system comprising:

one or more patient interfaces; and a processor configured to determine a duration of safe apnoea based on obtained information relating to an indicator.

In some configurations, the indicator is one or more of a respiratory indicator, and/or a physiological indicator.

In some configurations, the system may have any one or more of the features disclosed herein.

In some configurations, the processor is a remote processor.

Features from one or more embodiments may be combined with features of one or more other embodiments. Additionally, more than one embodiment may be used together during a process of respiratory support of a patient.

As relatively high gas delivery flow rates may be used with the embodiments or configurations described herein, the gases being supplied or delivered to the user or patient can may be delivered to different parts of the user's or a patient's airway.

For example, according to those various embodiments and configurations described herein, a flowrate of gases supplied or provided to an interface or via a system, such as through a flowpath, may comprise, but is not limited to, flows of at least about 5, 10, 20, 30, 40, 50, 60, 70, 80, 90, 100, 110, 120, 130, 140, 150 L/min (LPM), or more, and useful ranges may be selected between any of these values (for example, between about 40 LPM to about 80 LPM, or between about 50 LPM to about 80 LPM, or between about 60 LPM to about 80 LPM, or between about 70 LPM to about 80 LPM, or between about 5 LPM and about 150 LPM, or between 10 LPM and about 150 LPM, or between about 15 LPM and about 150 LPM, or between about 20 LPM and about 150 LPM, or between about 20 LPM and about 120 LPM, or between about 30 LPM and about 120 LPM, or between about 20 LPM and about 100 LPM, or between about 20 LPM and about 90 LPM, or between about 25 LPM and about 85 LPM, or between about 30 LPM and about 80 LPM or between about 30 LPM and about 90 LPM, or between about 35 LPM and about 75 LPM, or between about 40 LPM and about 70 LPM, or between about 45 LPM and about 65 LPM, or between about 50 LPM and about 60 LPM).

Such relatively high flowrates of gases may assist in providing the supplied gases into a user's airway, or to different parts of a user's airway, for example such flowrates may allow for a delivery of such gases to the upper or lower airway regions. Upper airway region typically includes the nasal cavity, pharynx and larynx, while the lower airway region typically includes the trachea, primary bronchi and lungs.

It should be understood that alternative embodiments may comprise any or all combinations of two or more of the parts, elements or features illustrated, described or referred to in this specification.

BRIEF DESCRIPTION OF THE DRAWINGS

Specific embodiments and modifications thereof will become apparent to those skilled in the art from the detailed description herein having reference to the figures that follow, of which.

DETAILED DESCRIPTION OF SPECIFIC EMBODIMENTS

Figure 1:
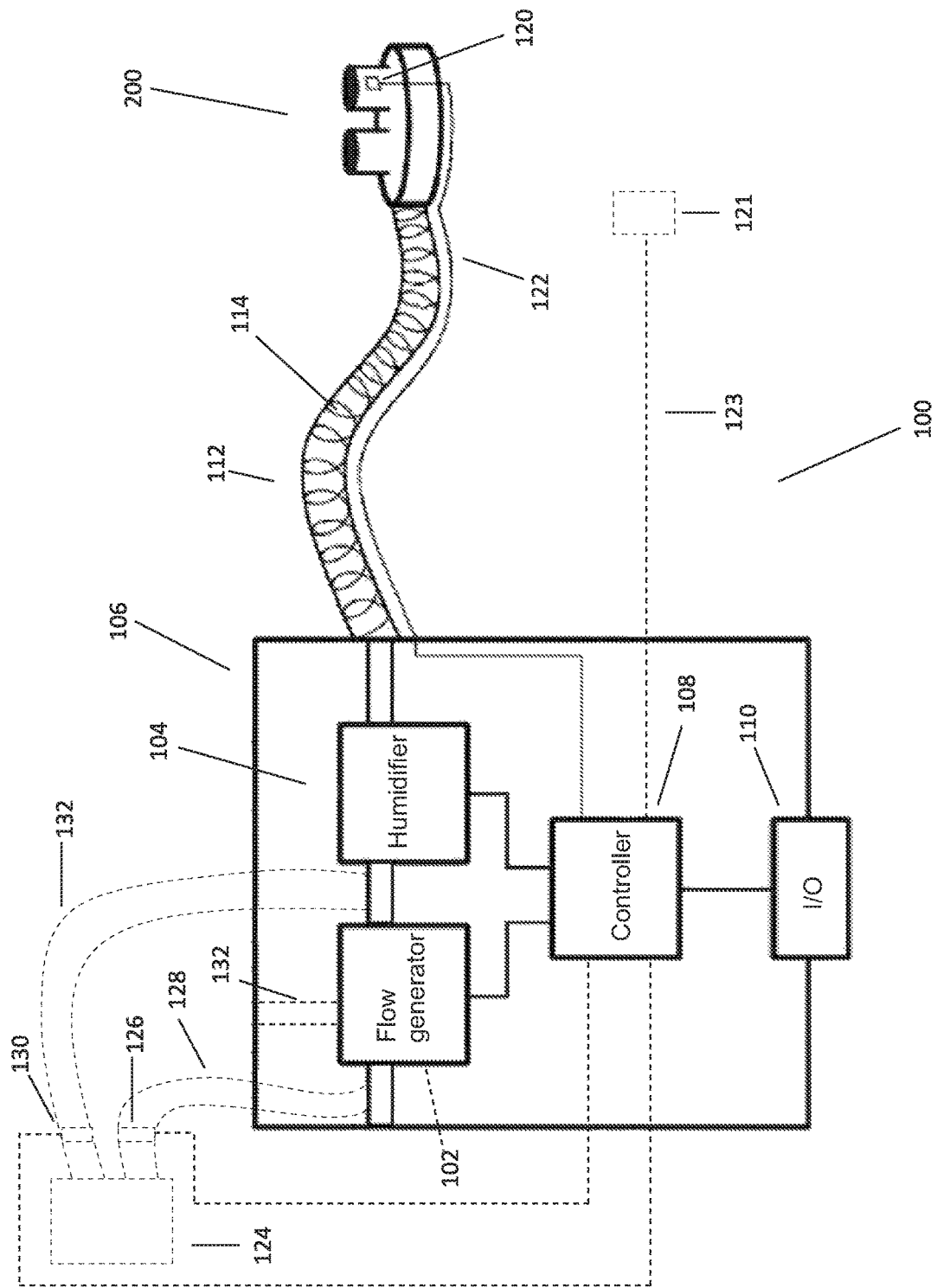
FIG. 1 shows a respiratory therapy system.

With reference to the non-limiting exemplary embodiment shown in FIG. 1, a respiratory therapy system 100 is shown. The respiratory therapy system 100 comprises a flow generator 102. The flow generator 102 is configured to generate gas flows that are passed through the respiratory therapy system 100. The flow generator 102 passes the air to a humidifier 104. The humidifier 104 is configured to heat and humidify gas flows generated by the flow generator 102. In some configurations, the flow generator 102 comprises a mechanical blower adapted to receive gases from the environment outside of the respiratory therapy system 100 and propel them through the respiratory therapy system 100. In some configurations the flow generator may deliver a flow of gases which is oscillating or has oscillating components. In some configurations, the flow generator 102 may comprise some other gas generation means. For example, in some configurations, the flow generator 102 may comprise one or more containers of compressed air and/or another gas and one or more valve arrangements adapted to control the rate at which gases leave the one or more containers. As another example, in some configurations, the flow generator 102 may comprise an oxygen concentrator. In some configurations, the flow generator 102 may be adapted to deliver a high flow therapy. 'High flow therapy' as used in this disclosure may refer to delivery of gases to a patient at a flow rate of greater than or equal to about 10 litres per minute (10 LPM). In some configurations, 'high flow therapy' may refer to the delivery of gases to a patient at a flow rate of between about 10 LPM and about 100 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. 'High flow therapy' may also for example, according to various embodiments and configurations described herein, be a flowrate of gases supplied or provided to an interface or via a system, such as through a flow path, but is not limited to, flows of at least about 5, 10, 20, 30, 40, 50, 60, 70, 80, 90, 100, 110, 120, 130, 140, 150 L/min (LPM), or more, and useful ranges may be selected between any of these values (for example, between about 40 LPM to about 80 LPM, or between about 50 LPM to about 80 LPM, or between about 60 LPM to about 80 LPM, or between about 70 LPM to about 80 LPM, or between about 5 LPM and about 150 LPM, or between 10 LPM and about 150 LPM, or between about 15 LPM and about 150 LPM, or between about 20 LPM and about 150 LPM, or between about 20 LPM and about 120 LPM, or between about 30 LPM and about 120 LPM, or between about 20 LPM and about 100 LPM, or between about 20 LPM and about 90 LPM, or between about 25 LPM and about 85 LPM, or between about 30 LPM and about 80 LPM or between about 30 LPM and about 90 LPM, or between about 35 LPM and about 75 LPM, or between about 40 LPM and about 70 LPM, or between about 45 LPM and about 65 LPM, or between about 50 LPM and about 60 LPM).

Gases delivered may comprise a percentage of oxygen. In some configurations, the percentage of oxygen in the gases delivered may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%.

High flow therapy has been found effective in meeting or exceeding the patient's normal peak inspiratory demand, to increase oxygenation of the patient and/or reduce the work of breathing. Additionally, high flow therapy may generate a flushing effect in the nasopharynx such that the anatomical dead space of the upper airways is flushed by the high incoming gas flows. This creates a reservoir of fresh gas available of each and every breath, while minimising re-breathing of carbon dioxide, nitrogen, etc.

Figure 9:
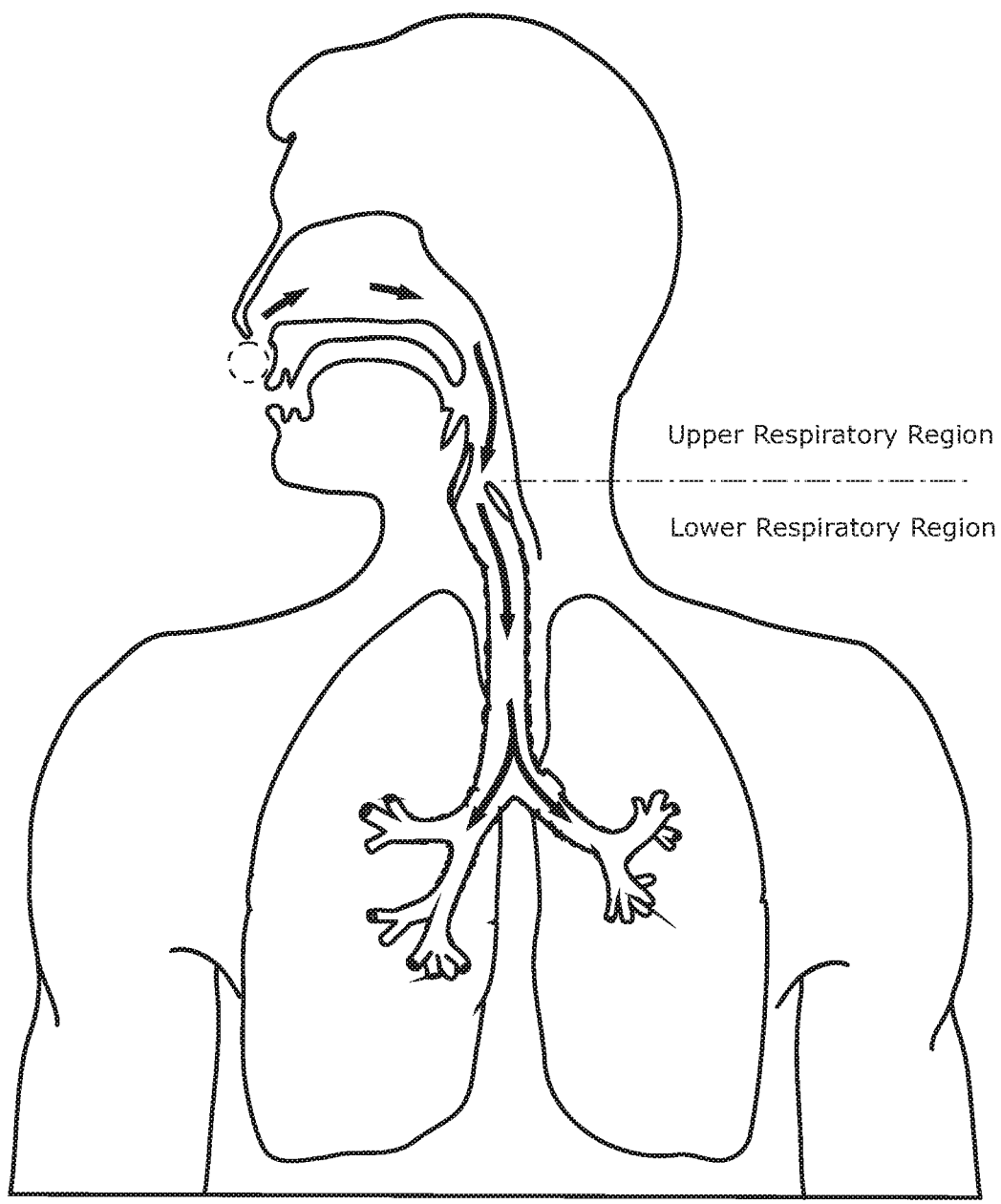
FIG. 9 shows a typical airway of a person, and includes arrows to indicate how a relatively high flowrate of gases supplied to a user may be utilised to effectively push or drive the supplied gases further or deeper into a user's airway than when the person is under normal or typical self-driven respiratory conditions.

FIG. 9 shows a typical airway of a person, and shows the direction of inward airflow during a patient's normal breathing. The arrows also indicate how a relatively high flowrate of gases supplied to a user may be utilised to effectively push or drive the supplied gases further or deeper into a user's airway than when the user is receiving a low flow rate of gases, or when the patient is apnoeic.

The respiratory therapy system 100 comprises a housing 106 that at least partially houses both the flow generator 102 and the humidifier 104 (e.g. the respiratory therapy system 100 may comprise an integrated flow generator/humidifier apparatus). In other configurations the flow generator 102 and humidifier 104 may have separate housings. The humidifier will provide the benefit of reducing drying of airways. However, the humidifier is optional, and the delivered gases do not need to be humidified. A hardware controller 108 is shown to be in electronic communication with the flow generator 102 and the humidifier 104, although in some configurations the hardware controller 108 might only communicate with the flow generator 102 or the humidifier 104. The hardware controller 108 may comprise a microcontroller or some other architecture configured to direct the operation of controllable components of the respiratory therapy system 100, including but not limited to the flow generator 102 and/or the humidifier 104. An input/output module 110 is shown to be in electronic communication with the controller 108. The input/output module 110 may be configured to allow a user to interface with the controller 108 to facilitate the control of controllable components of the respiratory therapy system 100, including but not limited to the flow generator 102 and/or the humidifier 104, and/or view data regarding the operation of the respiratory therapy system 100 and/or its components. The input/output module 110 might comprise, for example, one or more buttons, knobs, dials, switches, levers, touch screens, speakers, displays and/or other input or output peripherals that a user might use to view data and/or input commands to control components of the respiratory therapy system 100.

As further shown in FIG. 1, a supplementary gas source 124 may be used to add one or more supplementary gases to the gases flowing through the respiratory therapy system 100. The one or more supplementary gases join the gas flow generated by the flow generator 102. The supplementary gas source 124 may be configured to deliver one or more supplementary gases including but not limited to air, oxygen ($O_2$), carbon dioxide ($CO_2$), nitrogen ($N_2$), nitrous oxide (NO), and/or helix (a mixture of helium and oxygen). The supplementary gas source 124 may deliver the one or more supplementary gases via a first supplementary gas lumen 128 to a location upstream of the flow generator 102, and/or may deliver the one or more supplementary gases via a second supplementary gas conduit 132 to a location downstream of the flow generator 102 and/or upstream of the humidifier 104. One or more supplementary flow valves 126, 130 may be used to control the rates at which the one or more supplementary gases can flow from the supplementary gas source 124 and through the first and/or second supplementary gas conduits 128, 132. One or more of the supplementary flow valves 126, 130 may be in electronic communication with the controller 108, which may in turn control the operation and/or state of the one or more of the supplementary flow valves 126, 130. In other configurations, the supplementary gas source 124 may be configured to add one or more supplementary gases downstream of the humidifier 104. The supplementary gas source may be delivered by an independent system that is not used with the same flow generator 102. The supplementary gas source may be used in an anaesthetic gas delivery system which has an independent flow generator, and the gas is circulated.

As shown in FIG. 1, a conduit 112 extending from the humidifier 104 links the humidifier 104 to a patient interface 200. The conduit 112 may comprise a conduit heater 114 adapted to heat gases passing through the conduit 112. In other configurations the conduit heater 114 may not be present. The patient interface 200 is shown to be a nasal cannula, although it should be understood that in some configurations, other patient interfaces may be suitable. For example, in some configurations, the patient interface 200 may comprise a sealing or non-sealing interface, and may comprise a nasal mask, an oral mask, an oro-nasal mask, a full face mask, a nasal pillows mask, a nasal cannula, an endotracheal tube, a combination of the above or some other gas conveying system. In a preferred embodiment, the patient interface 200 is a non-sealing interface such as a nasal cannula, which allows gases to be exchanged with the environment. For example, the non-sealing cannula allows carbon dioxide to be removed and/or cleared from the patient's airways while the patient receives flow therapy from the system 100. Further, in the preferred embodiment, the patient interface 200 is in the form of a nasal interface, such that the system does not interfere with other oral airway equipment and/or devices, for example, a tracheal tube in an intubation procedure. Accordingly, the patient may continue to receive flow therapy throughout the intubation procedure.

As shown, in some configurations the patient interface 200 may also comprise a gas sensing module 120 adapted to measure a characteristic of gases passing through the patient interface 200. In other configurations the gas sensing module 120 could be positioned and adapted to measure the characteristics of gases at or near other parts of the respiratory therapy system 100. An example of such a configuration involves the gas sensing module 120 being located within the housing 106. The gas sensing module 120 may comprise one or more sensors adapted to measure various characteristics of gases, including but not limited to pressure, flow rate, temperature, absolute humidity, relative humidity, enthalpy, gas composition, oxygen concentration, carbon dioxide concentration, and/or nitrogen concentration. Gas properties determined by the gas sensing module 120 may be utilized in a number of ways, including but not limited to closed loop control of parameters of the gases. For example, in some configurations flow rate data taken by a gas sensing module 120 may be used to determine the instantaneous flow, which in turn may be used to determine the respiratory cycle of the patient to facilitate the delivery of flow in synchronicity with portions of the respiratory cycle. The gas sensing module 120 may communicate with the controller 108 over a first transmission line 122. In some configurations, the first transmission line 122 may comprise a data communication connection adapted to transmit a data signal. The data communication connection could comprise a wired data communication connection such as but not limited to a data cable, or a wireless data communication connection such as but not limited to Wi-Fi or Bluetooth. In some configurations, both power and data may be communicated over the same first transmission line 122. For example, the gas sensing module 120 may comprise a modulator that may allow a data signal to be 'overlaid' on top of a power signal. The data signal may be superimposed over the power signal and the combined signal may be demodulated before use by the controller 108. In other configurations the first transmission line 122 may comprise a pneumatic communication connection adapted to transmit a gas flow for analysis at a portion of the respiratory therapy system 100.

Additionally as shown a physiological sensor module 121 may be present. The physiological sensor module 121 may be configured to detect various characteristics of the patient or of the health of the patient, including but not limited to heart rate, blood pressure, EEG signal, EKG/ECG signal, blood oxygen concentration or a parameter relating to blood oxygen concentration (via, for example, a pulse oximeter or a direct sensing line), blood $CO_2$ concentration, transcutaneous $CO_2$ ($TcCO_2$) or $O_2$ (TcO2), expelled $CO_2$ or $O_2$, oxygen saturation via, for example, a pulse oximeter or a direct sensing line, and/or blood glucose. Similarly, the physiological sensor module 121 may communicate with the controller 108 over a second transmission line 123. The second transmission line 123 may comprise wired or wireless data communication connections similarly to the first transmission line 122, and power and data may be communicated similarly. The physiological sensor module 121 may be used, for example, to determine the blood oxygen saturation of the patient.

Figure 2:
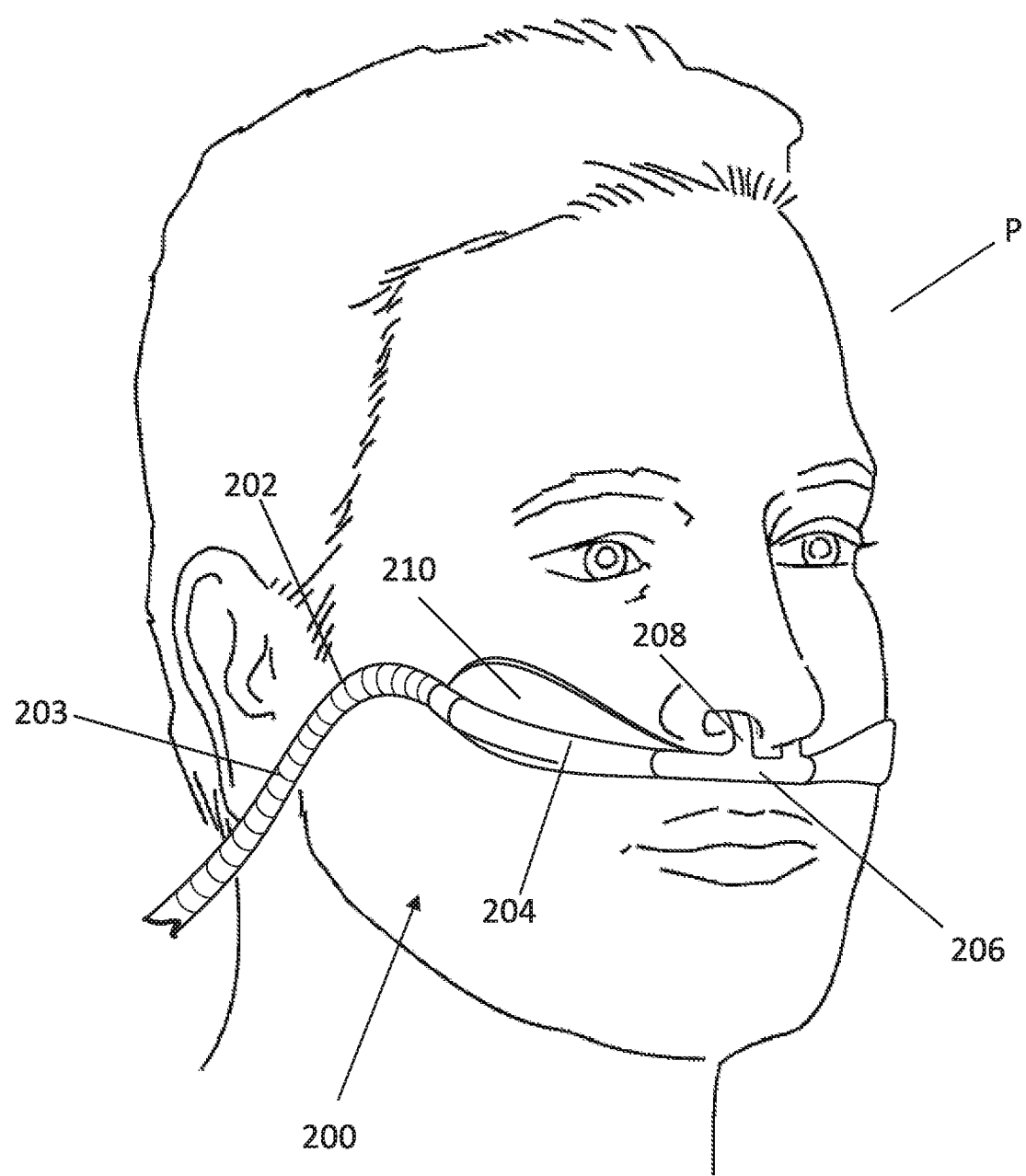
FIG. 2 shows a patient wearing a patient interface.

FIG. 2 shows a patient P wearing a patient interface 200. In the illustrated non-limiting configuration, the patient interface 200 is a nasal cannula. The patient interface 200 comprises a first gas lumen 202 defined by a tubular wall. The first gas lumen 202 is adapted to receive gases from the respiratory therapy system 100 (for example, via the conduit 112 shown in FIG. 1) and channel the gases to the patient P.

The illustrated first gas lumen 202 is defined at least in part by a wall within which gases can be channeled. The first gas lumen 202 may comprise a reinforcement element 203 adapted to strengthen and/or add rigidity to the first gas lumen to prevent deformation or collapse of the first gas lumen 202 arising due to the application of forces against the first gas lumen 202. The reinforcement element 203 may include a number of structures, including but not limited to plastic or metallic reinforcing beads that lie in or on the wall of the first gas lumen 202.

The first gas lumen 202 is in pneumatic communication with a flow manifold 206. The flow manifold 206 receives gases from the first gas lumen 202 and passes them to one or more nasal delivery elements 208 (e.g. prongs). The one or more nasal delivery elements 208 extend outwardly from the flow manifold 206. The one or more nasal delivery elements 208 are adapted to be non-sealingly positioned in one or more nares of the patient P. As shown, the patient interface 200 comprises two nasal delivery elements 208 adapted to be positioned one in each of the patient's nares. Each nasal delivery element 208 may be shaped or angled such that it extends inwardly towards a septum of the patient's nose.

Additionally, each nasal delivery element may be shaped or angled such that a tip of each nasal delivery element points, in use, towards a back of the head of the patient P. In the embodiment shown in FIG. 2, the flow manifold 206 receives flow from one lateral side of the flow manifold 206 (e.g. with respect to an imaginary vertical plane bisecting the face of the patient P) and channels flow to each of the nasal delivery elements 208. In other configurations, the patient interface 200 may comprise greater (for example, three or four) or fewer (for example, one) nasal delivery element 208.

In other configurations, each nasal delivery elements 208 can have different properties. For example, one of a pair of nasal delivery elements 208 can be relatively long and the other nasal delivery element 208 can be relatively short. In some configurations, the flow manifold 206 may be configured to receive flow from two lateral sides of the flow manifold 206 (e.g. from a 'left' and 'right' of the flow manifold 206 when instead of just the 'left' of the flow manifold 206 as seen in FIG. 2). In some such configurations, multiple gas lumens may be used to provide for pneumatic communication between the flow manifold 206 and the respiratory therapy system 100. In some configurations, the flow manifold 206 may be configured to receive flow from a non-lateral side of the flow manifold 206 (e.g. from a 'bottom' or 'top' of the flow manifold 206).

The patient interface may further comprise mounts and/or supports, e.g., cheek supports 210, for attaching and/or supporting the gas lumen 202 on the patient's face. Additionally, the patient interface may comprise a headgear or head straps to attach and/or support the patient interface 200 (including the gas lumen 202) on the patient's face.

Figure 3:
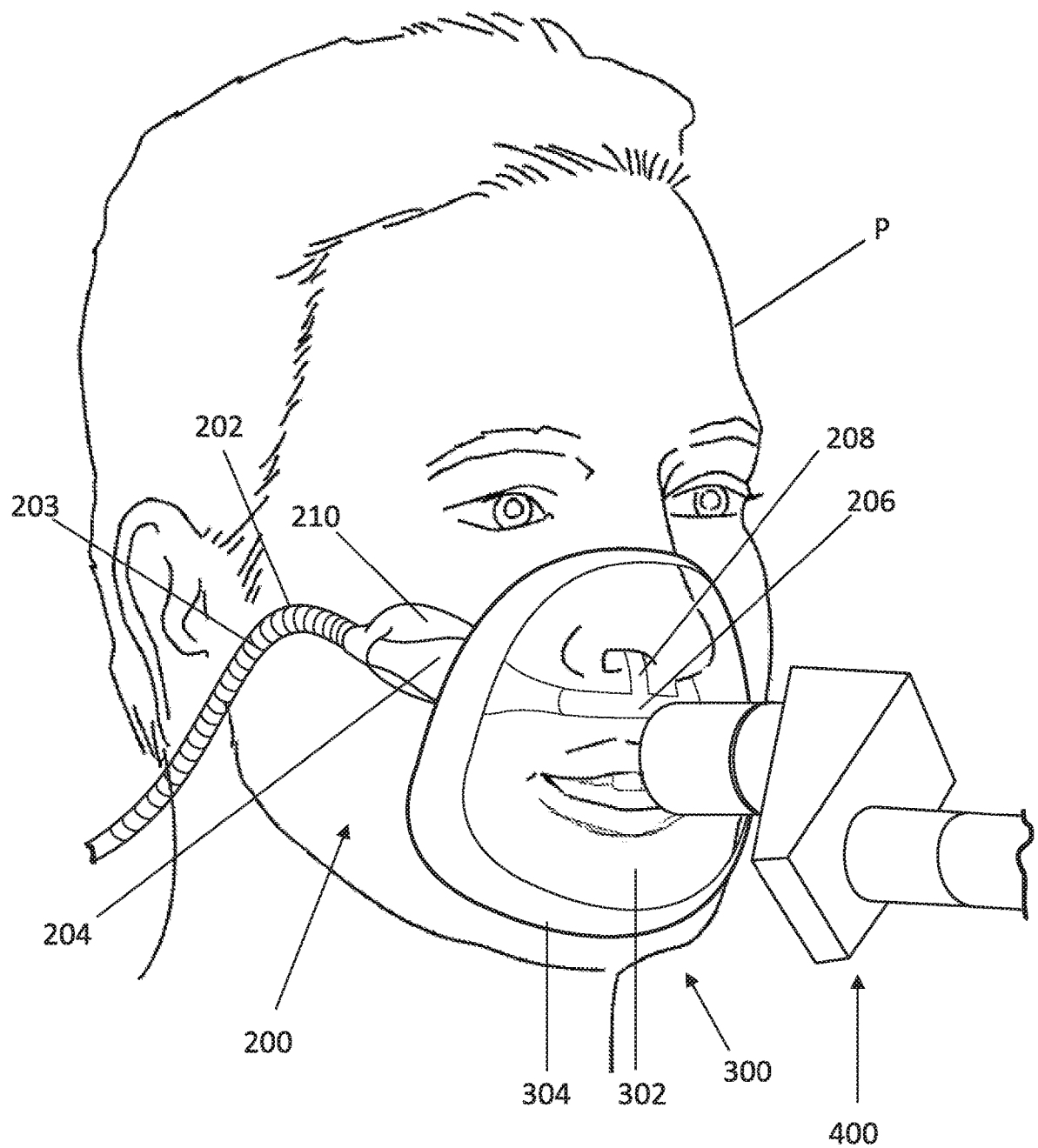
FIG. 3 shows a patient wearing a patient interface and a face mask.

FIG. 3 shows a non-limiting exemplary embodiment of a patient P wearing the patient interface 200 as shown in FIG. 2 underneath a face mask 300 assembly. FIG. 3 schematically shows the face mask as a transparent structure in order to illustrate the patient interface 200 under it.

Face mask assembly 300 may be used as a second respiratory support subsystem and/or to deliver one or more other substances, for example anaesthetic agents, to the patient. Accordingly, the embodiment shown in FIG. 3 allows for the delivery of gas from multiple sources via two respiratory support subsystems. Additionally, this configuration may allow the patient interface 200 to be left on the patient throughout the surgical procedure and/or into recovery (whether or not the patient continues to receive flow therapy through the patient interface 200 throughout the procedure).

In the embodiment shown, face mask assembly 300 comprises a full face mask 302 configured to cover both the patient's nose and mouth. In other configurations, the face mask 300 may be a nasal mask which is placed over the patient interface 200 to cover only the patient's nasal region.

As shown, the face mask 302 comprises a seal region 304 adapted to seal against the patient's face. The face mask assembly 300 is connected to a second gas source 400 which supplies the one or more other gases to the patient via the face mask. That is, gas source 400 is preferably different from the source supplying gas (for example, supplementary gas source 124) to the patient interface 200.

In a preferred embodiment, the face mask assembly 300 is connected to a separate gas source 400 or a separate respiratory support device. For example, the respiratory support can be a ventilator or a CPAP or a high flow therapy device.

Alternatively the mask assembly 300 could be connected to an anaesthetic device and anaesthetic gas can be delivered via the mask 302.

The preferred embodiment, as exemplified in FIG. 3, allows for the delivery of gas from multiple sources via at least two different respiratory support modes, and further allows a doctor, clinician or medical professional to quickly and easily change the type of respiratory support mode.

With the advent of nasal high flow and its intended use in the anaesthesia setting the user of the system would want an estimate for how long an apnoeic period would be safe. The following embodiments relate to different methods for monitoring an apnoeic period and predicting or determining the duration of safe apnoea. It should be noted these methods are not exclusive to anaesthesia and nasal high flow. The methods could also be used for apnoeic periods in a general respiratory setting and/or when different respiratory support mechanisms are used.

The following embodiments may be used to pre-predict a duration of safe apnoea before apnoea occurs and/or may be used to monitor or record apnoea trends during apnoea. The embodiments will be performed by one or more processors. The processor may be the hardware controller 108 of the respiratory therapy system 100. Alternatively, the processor may be one or more other hardware processors. Alternatively, the embodiments may be performed by the controller along with one or more other processors.

The embodiments comprise obtaining information relating to one or more indicators (such as a respiratory indicator and/or a physiological indicator), and determining a duration of safe apnoea from the obtained information. Where the term 'indicator' is used, reference to 'indicator' may refer to either or both of a respiratory indicator and/or a physiological indicator.

Figure 4:
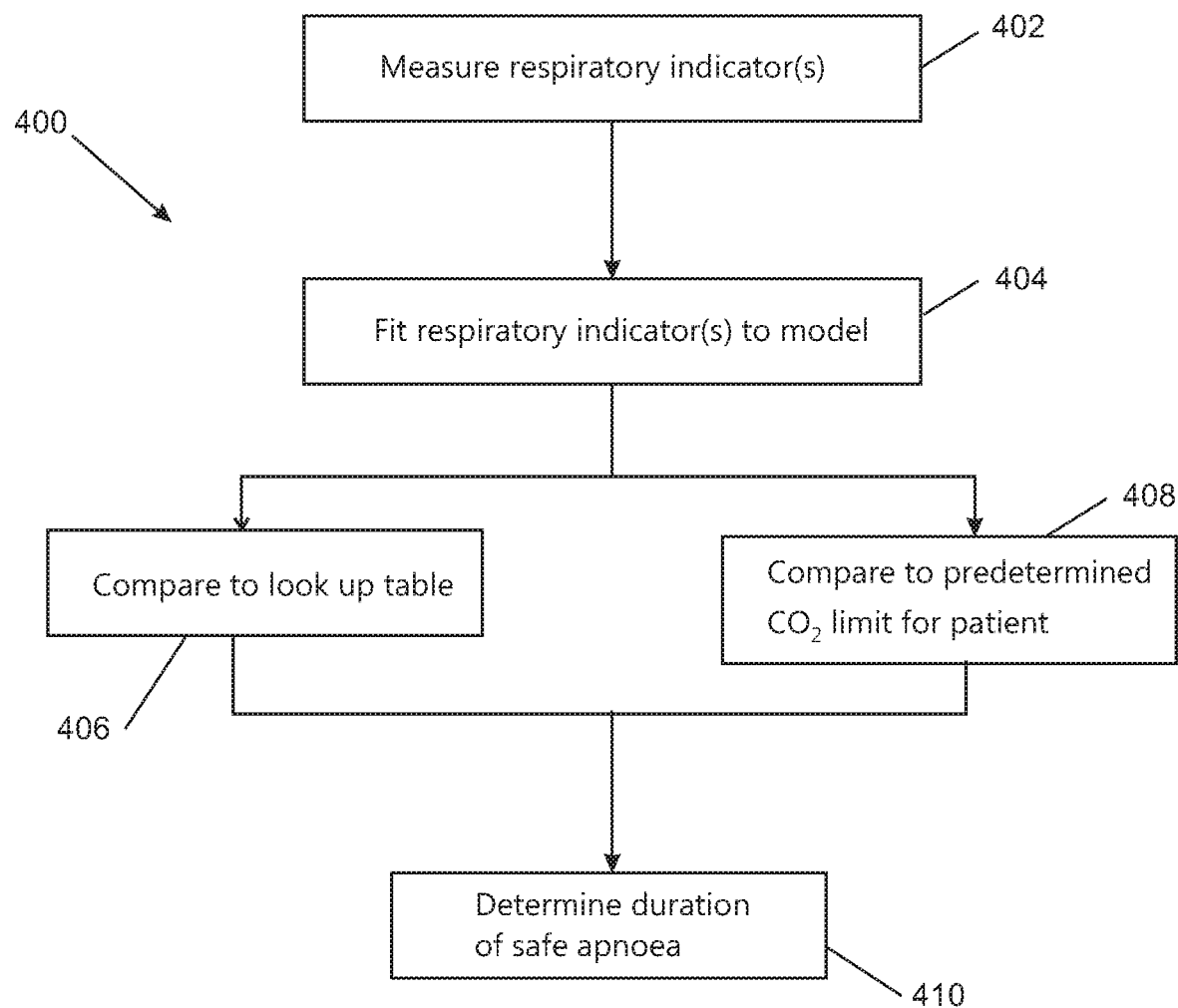
FIG. 4 is a flow chart schematically showing a first method of predicting or determining duration of safe apnoea.
Figure 5:
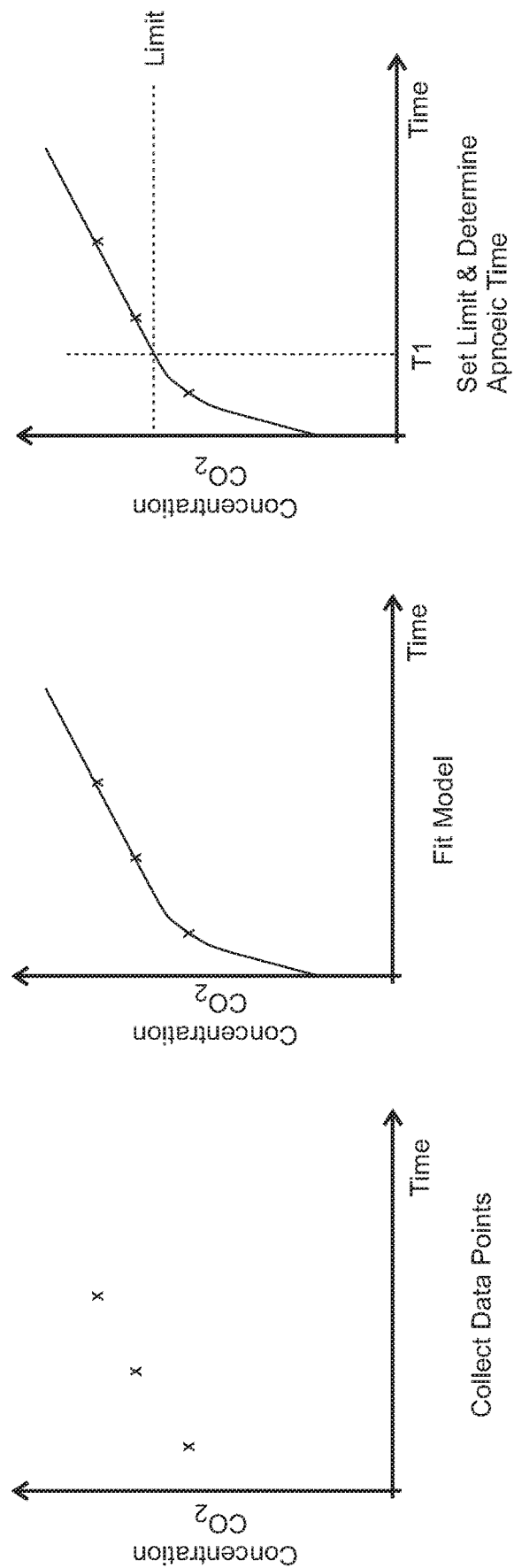
FIG. 5 shows plots representing various stages of the method of FIG. 4.

The respiratory therapy system comprises one or more patient interfaces, and a processor configured to determine a duration of safe apnoea based on obtained information relating to one or more respiratory indicators. Additionally, or alternatively the processor may be configured to determine a duration of safe apnoea based on obtained information relating to one or more physiological indicators FIGS. 4 and 5 schematically show a first embodiment method 400 for predicting or determining a duration of safe apnoea. In a first step 402, this method comprises measuring an indicator of a patient. The indicator may be any suitable indicator such as carbon dioxide concentration, carbon dioxide clearance, respiratory rate, oxygen concentration, arterial oxygen, arterial carbon dioxide content, lung volume, lung compliance, lung/airway pressure, airway resistance/patency, V/Q mismatch (ventilation (V)-perfusion (Q)), heart rate, blood pressure, or metabolic rate for example. Additionally, a parameter relating to the opening of alveoli may be measured. The indicator (such as a respiratory indicator and/or a physiological indicator) may be measured by one or more suitable sensors, which may be the sensors 120, 121 in the respiratory therapy system or may be additional or alternative sensors. The measurements from the sensor(s) may be recorded automatically by the processor 108, or may be recorded by an operator and input to the processor via a user interface such as a keyboard or touch screen.

In apnoea, there is a reduced capacity for carbon dioxide ($CO_2$) to be removed from the lungs and it accumulates in the blood, or there is not enough oxygen being supplied to the lungs and/or blood. A greater lung volume generally means a greater presence of $O_2$ which should result in a longer duration of safe apnoea. Lung volume may be measured by electrical impedance tomography (EIT) or another method. Measuring the patient's carbon dioxide and comparing or fitting a model to it may be used to determine the duration of safe apnoea. Such a process is shown schematically in FIG. 5. As shown in FIG. 5(*a*), a plurality of carbon dioxide concentration measurements are taken at different times. Carbon dioxide concentration may be measured based on expired carbon dioxide, transcutaneous carbon dioxide, or blood gases for example.

The processor determines the duration of safe apnoea from the measured indicator (such as a respiratory indicator and/or a physiological indicator), for example carbon dioxide. The processor 108 may compare or fit 404 the measured indicator to a model, as shown in FIG. 5(*b*).

Once compared or fit to the model, the processor 108 may determine the duration of safe apnoea based on a maximum carbon dioxide limit in the model. This is shown in FIG. 5(*c*). In one configuration 406, the processor may determine the maximum carbon dioxide limit from a look up table with predetermined different safe carbon dioxide limits. The processor may be pre-programmed with a look up table. Alternatively, the processor may access a look up table and perform a comparison with the look up table. The safe carbon dioxide limits in the look up table may be based on one or more of:

disease (for example chronic obstructive pulmonary disease, emphysema, asthma etc.)
age
height
weight
pregnancy status
difficult airway type
clinical history (for example, of acidosis).

In an embodiment, the safe carbon dioxide limit can be calculated in real time for a patient based on one or more of these parameters. These parameters may be inputted into the processor and used to calculate the safe carbon dioxide limit.

In another configuration 408, the maximum carbon dioxide limit in the model may be a predetermined maximum carbon dioxide limit for the specific patient. The maximum carbon dioxide limit may be entered to the processor via a user interface. The carbon dioxide limit may be a clinical parameter entered by a user for example a clinician. Alternative 408 may be used as a preferred option for a conscious patient, with alternative 406 used if the patient is unconscious.

The processor may then determine 410 the duration of safe apnoea based on the maximum carbon dioxide limit and the model. While the process shown in FIG. 5 has various plots, it will be appreciated by a skilled person that actual plots will not necessarily be provided, and the processor 108 may perform the method using suitable calculations and/or steps. However, the plots are analogous of the process that may be performed by the processor 108.

Instead of measuring carbon dioxide, the method may be performed based on a different indicator such as, respiratory rate, oxygen concentration, arterial oxygen or carbon dioxide content, lung volume, lung compliance, lung/airway pressure, airway resistance/patency, metabolic rate, V/Q mismatch (ventilation (V)-perfusion (Q)), heart rate, blood pressure, or metabolic rate. The steps of the method may correspond to those outlined above. When using measured oxygen concentration as the indicator, oxygen concentration may be measured based on expired oxygen, transcutaneous oxygen, blood gases, haemoglobin oxygen concentration, blood pressure, arterial partial pressure of oxygen, or arterial oxygen content. Arterial oxygen content may be determined as (haemoglobin concentration x 1.34×arterial oxygen saturation)+(0.0031×partial pressure of oxygen).

V/Q mismatch, also known as shunt, occurs if gas exchange doesn't take place when blood goes past the lungs. This may lead to $CO_2$ accumulating in the blood and/or not enough $O_2$ in the blood. V/Q mismatch is caused by anything that increases or decreases ventilation or perfusion of the lungs. This may occur due to gravity or due to a certain blood flow pattern or from atelectasis. If the oxygen being delivered to a patient is increased but more oxygen is not appearing in the blood, then this indicates there is a V/Q mismatch.

Alternatively, the method may comprise measuring a plurality of indicators, for example one or more respiratory indicators and/or physiological indicators of the patient.

The plurality of indicators may comprise two or more of carbon dioxide concentration or carbon dioxide clearance, respiratory rate, oxygen concentration, arterial oxygen or carbon dioxide content, lung volume, lung compliance, lung/airway pressure, airway resistance/patency, V/Q mismatch (ventilation (V)-perfusion (Q)), heart rate, blood pressure, or metabolic rate. For example, carbon dioxide may be measured in addition to one or more of the listed indicators.

When a plurality of indicators are measured, the processor may determine an average duration of safe apnoea from the plurality of measured indicators. Alternatively, the processor may determine a plurality of durations of safe apnoea from the plurality of measured respiratory indicators and/or measured physiological indicators and the processor may then be configured to select the shortest duration of safe apnoea from the plurality of measured respiratory indicators.

Figure 6:
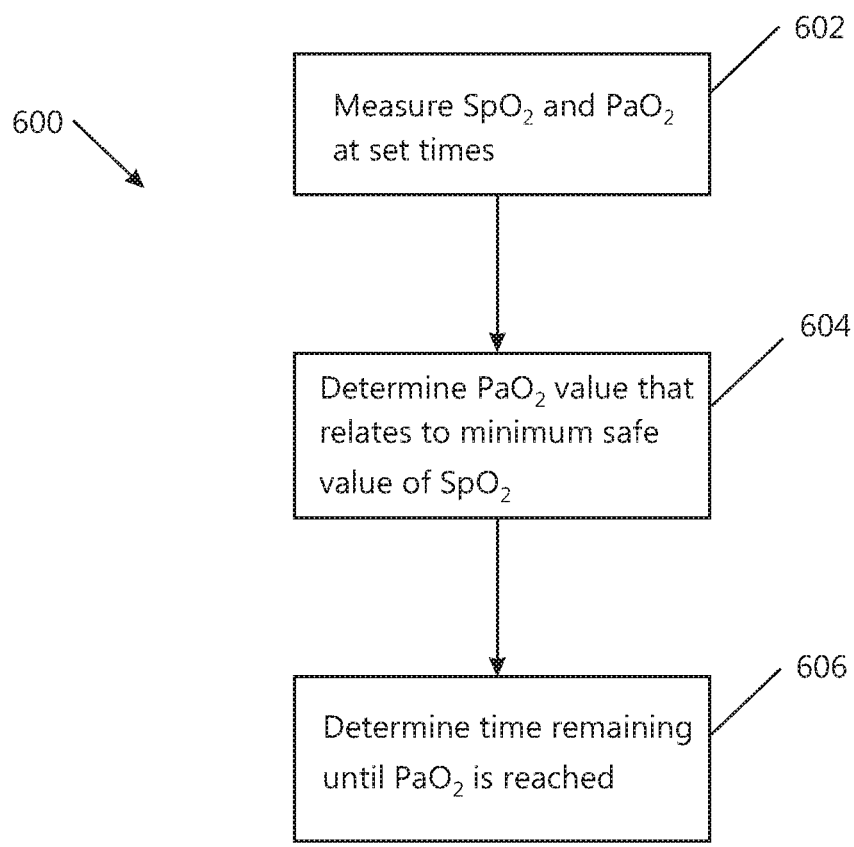
FIG. 6 is a flow chart schematically showing a second method of predicting or determining a duration of safe apnoea.

FIG. 6 schematically shows a second embodiment method 600 for predicting or determining a duration of safe apnoea. This method comprises determining a duration of safe apnoea based on a relationship between a patient's haemoglobin oxygen saturation ($SpO_2$) and arterial partial pressure of oxygen ($PaO_2$). In an anaesthetised patient, the oxygen consumption remains fairly constant. This oxygen is delivered to the tissues by haemoglobin. The oxygen in the haemoglobin is then replenished, on return to the pulmonary circulation, by the diminishing store of oxygen within the lungs. The haemoglobin oxygen saturation remains greater than 90% as long as the haemoglobin can be re-oxygenated in the lungs. The $SpO_2$ only starts to decrease when the store of oxygen in the lungs is depleted. However the $PaO_2$ decreases in direct relation to the diminishing store of oxygen within the lungs.

Figure 6A:
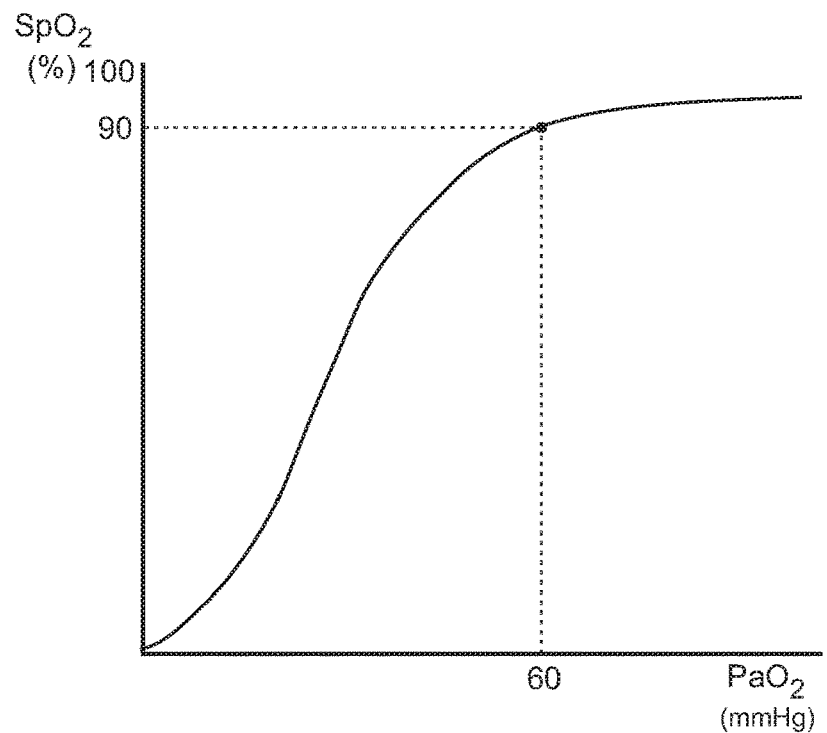
FIG. 6A is a graph showing the relationship between $SpO_2$ to $PaO_2$.

An oxyhaemoglobin dissociation curve mathematically equates $SpO_2$ to $PaO_2$. A typical curve showing the relationship between $SpO_2$ to $PaO_2$ is shown in FIG. 6A. As the duration of a safe apnoea can be defined by the de-saturation, a patient specific dissociation curve can be used to estimate the relationship between $SpO_2$ to $PaO_2$ and the remaining safe apnoea time. A threshold $SpO_2$ may be input by a clinician or determined based on a particular patient and or their characteristics. The $SpO_2$ threshold may correspond with the safe threshold of $SpO_2$ for a patient, below which a patient will be considered to have desaturated. The $SpO_2$ threshold may be for example 90% (as for example shown in FIGS. 6A and 6B).

Figure 6B:
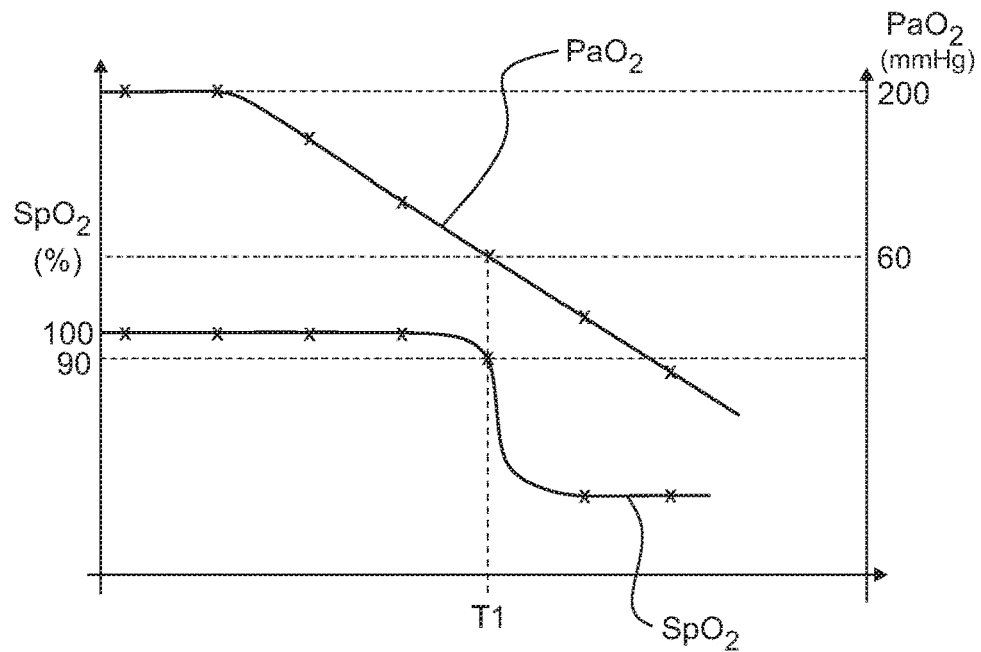
FIG. 6B is a graph showing the variance of $PaO_2$ and $SpO_2$ over time.

FIG. 6B shows $PaO_2$ and $SpO_2$ over time during an apnoea event as may be for example measured by method 600. FIG. 6B shows a patient with an initial $SpO_2$ of about 100%, and an initial $PaO_2$ of about 200 mmHg. Once the apnoea event begins the patient's $PaO_2$ decreases as oxygen is consumed but not replaced. FIG. 6B shows that even though $PaO_2$ is decreasing no corresponding decrease in $SpO_2$ is initially observed. Once a decrease of $SpO_2$ is observed it can often be too late, and the patient can desaturate rapidly. Further, due to the rapid decrease of $SpO_2$ no warning of patient desaturation is provided.

In some configurations, the safe apnoea time may be based on a threshold arterial partial pressure of oxygen ($PaO_2$). The threshold arterial oxygen content may be determined from a threshold haemoglobin oxygen saturation ($SpO_2$) as described above, and as shown in FIG. 6A. For example as shown in FIGS. 6A and 6B one example threshold haemoglobin oxygen saturation ($SpO_2$) is 90%, which corresponds to 60 mmHg $PaO_2$.

In some configurations, the duration of safe apnoea is based on, or may be equal to, a length of time until the arterial partial pressure of oxygen reaches (or optionally goes below) the threshold arterial partial pressure of oxygen. The length of time until the arterial partial pressure of oxygen reaches the threshold arterial partial pressure of oxygen may be determined by measuring or estimating a rate of change of arterial partial pressure of oxygen. For example in FIG. 6B the length of time until the arterial partial pressure of oxygen reaches the threshold arterial partial pressure of oxygen (or the duration of safe apnoea) is T1. At the time T1 the arterial partial pressure of oxygen may be 60 mmHG, which corresponds to a haemoglobin oxygen saturation ($SpO_2$) of 90%, as determined from FIG. 6A

In a first step 602, a patient's $SpO_2$ and $PaO_2$ are measured at set times. This generates a set of points on the dissociation curve, and a sigmoidal shape can then be fitted to the points. These data points and/or the resulting fitted curve may include correction factors for temperature, pH, PaCO2, and/or the characteristics of the patient's haemoglobin. Such correction factors address the left or right-hand shifts of the curve, also known as Bohr/Haldane shifts, as such shifts could significantly change the safe apnoea time.

The $SpO_2$ may be measured by or inferred from pulse oximetry. The $PaO_2$ may be measured using blood gases or by inferring the $PaO_2$ from a transcutaneous oxygen measurement, by pulse oximetry, or other methods known in the art.

The processor may then determine 604 an $PaO_2$ that relates to a specified minimum safe value of $SpO_2$. The minimum safe value of $SpO_2$ may be a predetermined value or alternatively may be a value that has been entered to the processor via a user interface. By way of example, the minimum safe value of haemoglobin oxygen saturation may be about 90%, may be 90%, between about 88% and about 90%, may be between 88% and 90%, or may be any suitable value as entered by a clinician or as determined from a look up table based on one or more patient characteristics such as:

- disease (for example chronic obstructive pulmonary disease, emphysema, asthma etc.)
- age
- height
- weight
- pregnancy status
- difficult airway type
- clinical history (for example, of acidosis).

The $PaO_2$ and/or $SpO_2$ may then be plotted against time (from the first step). Based on this relationship between the measured $PaO_2$ and/or SpO2, and time, the processor may then determine 606 the time remaining until the determined $PaO_2$ is reached, thereby determining the duration of safe apnoea. That may be achieved by the same method as the carbon dioxide method of the embodiment of FIGS. 4 and 5.

Additionally or alternatively, the method comprises determining the time remaining until the determined PaO2 value is reached, based on a rate of change of PaO2.

While the method is described with reference to forming curves, fitting a sigmoidal shape to the points, and plotting $PaO_2$ against time, it will be appreciated by a skilled person that actual curves, shape, and plots will not necessarily be provided, and the processor 108 may perform the method using suitable calculations and/or steps. However, the curves, shape, and plots are analogous of the process that may be performed by the processor 108.

Figure 7:
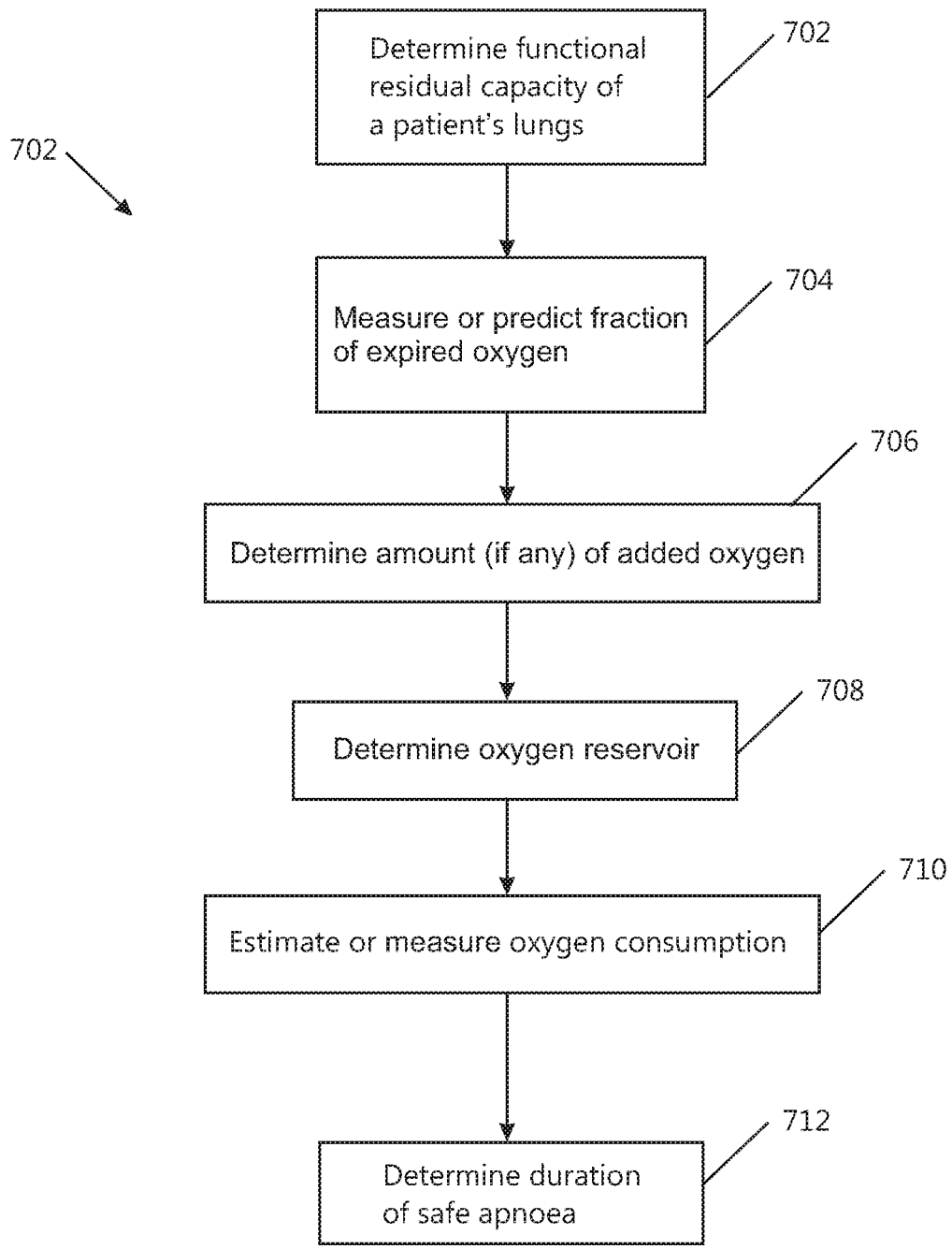
FIG. 7 is a flow chart schematically showing a third method of predicting or determining a duration of safe apnoea.

FIG. 7 schematically shows a third embodiment method 700 for predicting or determining a duration of safe apnoea. This method comprises determining a duration of safe apnoea based on a relationship between a patient's oxygen reservoir (for example, the amount of oxygen present in a patient's lungs) and their oxygen consumption.

The rate of oxygen de-saturation is influenced by the balance between the oxygen reservoir in the lungs and consumption, as outlined by the following equation:

$$\text{Time of safe apnoea} \sim \frac{\text{Oxygen reservoir}}{(\text{Oxygen consumption} - \text{Oxygen supplied})}$$

A first step 702 of the method comprises determining the functional capacity of a patient's lungs to determine a maximum oxygen reservoir volume. The step of determining the functional capacity may comprise estimating using one or more of nitrogen washout, helium dilution, body plethysmography, or a look up table. The step of determining the functional capacity may be performed by the processor or otherwise. The look up table may provide indicative functional reservoir values for different types of patients, for example a healthy patient may have a typical volume reservoir of 30 ml/kg and an obese patient may have a typical volume reservoir of 15 ml/kg.

A second step 704 of the method may comprise measuring or predicting the oxygen consumption of a patient. In some embodiments the oxygen consumption of a patient may be based on a volume of expired oxygen ($FeO_2$) or volume of $CO_2$ entering or exiting the patients airway, or in the patient's lungs. The oxygen consumption of a patient and/or the volume of expired oxygen may be influenced by pre-oxygenation level, age, weight, disease state, etc. The step of measuring or predicting may be performed by the processor or otherwise.

In some embodiments, any supplied oxygen may be shut off for a period of time, and the volume of expired or expelled oxygen ($FeO_2$), or expired or expelled carbon dioxide ($CO_2$) can be measured. In other embodiments, such measurements may be taken while oxygen continues to be supplied.

In some embodiments, the volume of expired oxygen ($FeO_2$) may be determined based on a measurement or estimation of metabolic rate of the patient. Additionally or alternatively, the volume of expired oxygen ($FeO_2$) may be determined based on a measurement or estimation of concentration or volume of $CO_2$ (optionally expelled or expired) at or near a patient's airway. Additionally or alternatively, the volume of expired oxygen ($FeO_2$, or expired carbon dioxide ($CO_2$)) may be determined based on a measurement or estimation of a flow sensor in the ventilation circuit. The flow sensor may output a flow signal indicative of a tidal flow of a patient's breathing pattern, optionally said flow signal may include a bias flow or provided flow component. Optionally, the known supplied or provided flow component can then be removed or filtered from the flow signal to provide a filtered flow signal indicative of a tidal flow of a patient's breathing pattern. From the flow signal indicative of a tidal flow of a patient's breathing pattern, the volume or amount of expired or expelled $CO_2$ and/or the volume or amount of expired or expelled oxygen ($FeO_2$) may be determined (optionally utilising the measurement of concentration of expelled or expired carbon dioxide ($CO_2$) at or near a patient's airway, and/or expelled or expired oxygen ($FeO_2$).

If any oxygen has been provided to the patient by the respiratory therapy system 100, a third step 706 may comprise determining the amount of additional oxygen provided to the patient and/or provided to the patient's lungs by the respiratory therapy system.

The processor may then determine 708 the patient's oxygen reservoir based on the maximum oxygen reservoir volume, less the volume of expired oxygen, plus the amount of oxygen provided to the patient by the respiratory therapy system, if any.

The processor may determine 710 the patient's oxygen consumption. This may be estimated based on the patient's weight ($=10 \times \text{Weight}^{3/4}$), may be measured, or may be determined using any other suitable method. It will be appreciated that this step may be carried out before, during, or after the other steps 702-708.

The processor may determine 712 the duration of safe apnoea based on the patient's determined oxygen reservoir divided by the patient's oxygen consumption.

Figure 8:
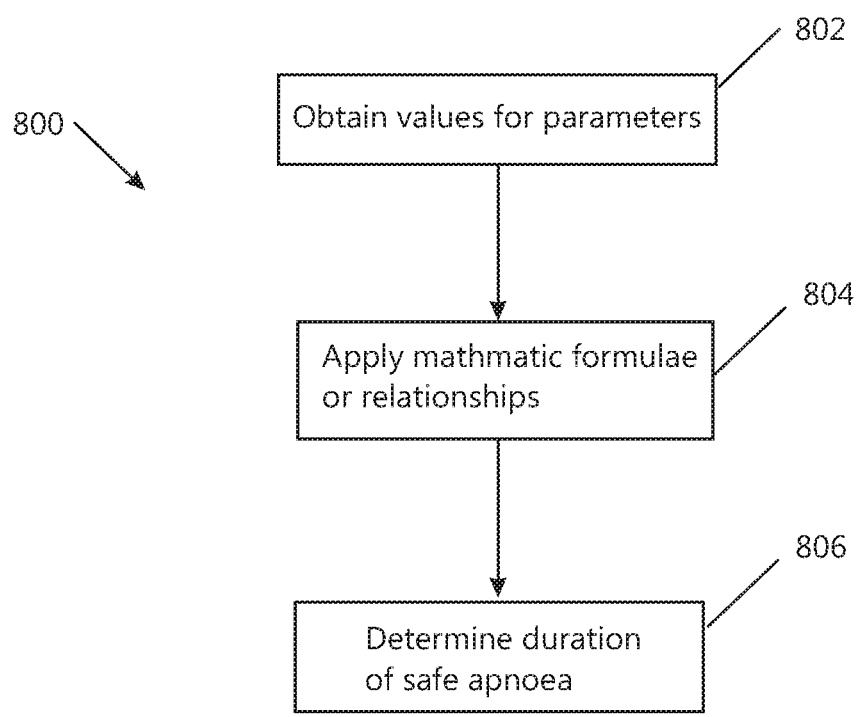
FIG. 8 is a flow chart schematically showing a fourth method of predicting or determining a duration of safe apnoea.

FIG. 8 schematically shows a fourth embodiment method 800 for predicting or determining a duration of safe apnoea. This method comprises determining a duration of safe apnoea based on one or more parameters relating to pre-oxygenation of a patient. The parameter(s) is/are indicative of the effort (i.e. ease or difficulty) to pre-oxygenate the patient to a desired level.

The parameter(s) may comprise one or more of:
i. the ratio of fraction of oxygen in expired air to the fraction of inspired oxygen $$\frac{F_eO_2}{F_iO_2}$$

ii. the ratio of haemoglobin oxygen saturation and fraction of inspired oxygen $$\frac{S_pO_2}{F_iO_2}$$

iii. the P/F ratio which is the ratio of arterial partial pressure of oxygen and fraction of inspired oxygen $$\frac{P_aO_2}{F_iO_2}$$

the ratio of peripheral venous oxygenation and peripheral arterial oxygenation $$\frac{P_vO_2}{P_aO_2}$$

v. the time required to pre-oxygenate the patient
vi. the patient's metabolic rate.
vii. the rate of rise of $PaO_2$ If $FeO_2$ indicates that it is easy to pre-oxygenate the patient, then this may suggest that there is V/Q mismatch. For example, if the $FeO_2$ increases, and the $SpO_2$ or $PaO_2$ does not increase, or does not increase at a corresponding rate, this suggests that oxygen is going into the lungs well, but not getting into the blood well, and could be an indicator that the patient will desaturate more quickly during an apnoeic event than an average healthy patient, and indicates that a shorter safe apnoea time is more suitable for that patient.

If $PaO_2$ indicates that it is easy to pre-oxygenate the patient (i.e. it rises well and quickly during pre-oxygenation), then this suggests a slow desaturation during an apnoea event because a lot of alveoli are open and good gas exchange is occurring, and therefore a longer safe apnoea time may be appropriate for that patient.

In a first step 802 of the method, values are obtained for the parameters that will be used. The values may be obtained by suitable measurement and/or estimation techniques, and may be obtained by the processor or otherwise.

In a second step 804 of the method, the processor applies one or more mathematical formulae or relationships or algorithms to determining the duration of safe apnoea.

Any of the above methods may be performed or calculated by the processor, or alternatively could be determined on a remote server and then sent to the processor to execute.

In any of the above methods, during respiratory therapy of a patient, the processor 108 may be configured to generate an alert based on the determined duration of safe apnoea. The alert may be a visual alert such as a warning light or a warning on a display unit, an audible alert such as an audible alarm, or a tactile alert such as a vibrating alert. Alternatively, the alert may be a combination of any of the above. The processor may generate the alert substantially at the end of the duration of safe apnoea, or at a specified time before the duration of safe apnoea, such as 10-15 seconds for example. The generation of the alert(s) will alert an anesthetist to the end of the safe apnoea period, to enable them to supply additional oxygen to the patient or induce breathing assistance to the patient.

In addition or alternatively, the processor 108 may be configured to supply additional oxygen to the patient or induce breathing assistance to the patient, based on the determined duration of safe apnoea. Again, that may occur substantially at the end of the duration of safe apnoea, or at a specified time before the duration of safe apnoea, such as 10-15 seconds for example. For example, the processor may be configured to cause oxygen to be delivered through one of the patient interfaces of the respiratory support system.

Figure 10:
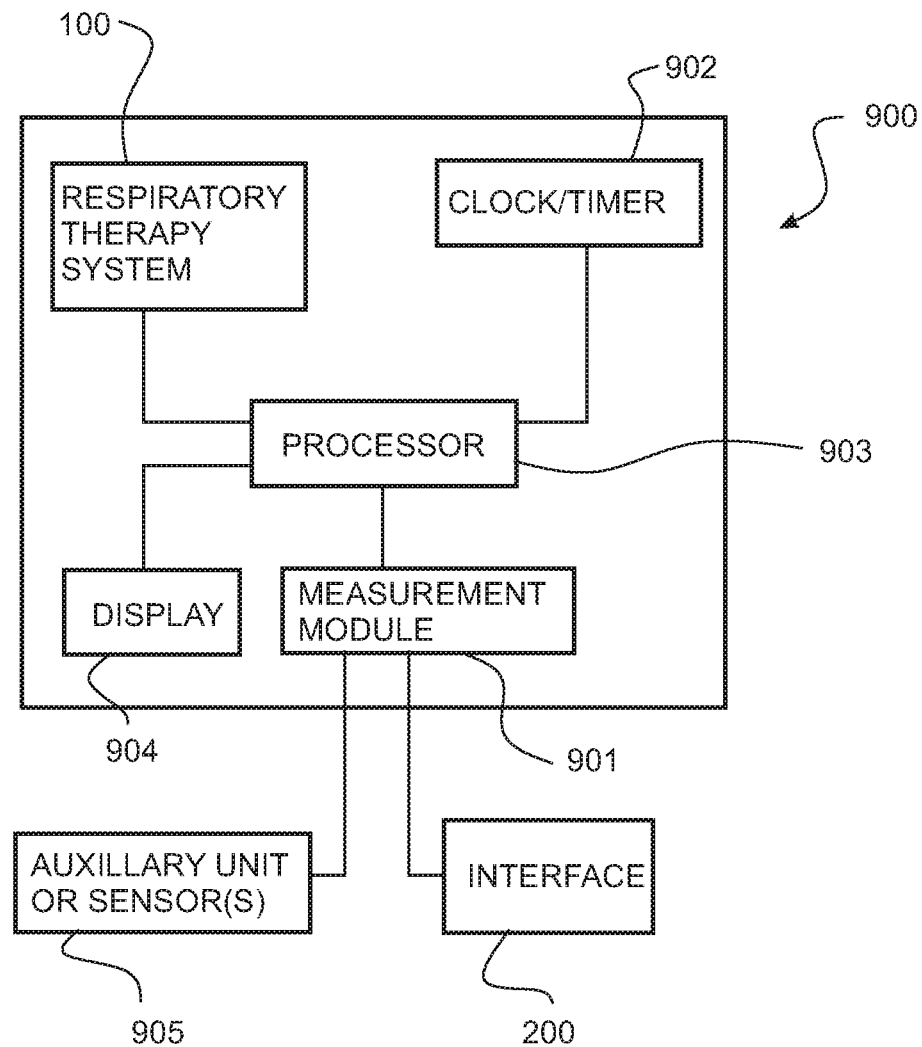
FIG. 10 shows an example apparatus.

FIG. 10 shows an example apparatus 900 for carrying out any of the methods as described above, and/or to be provided as part of a system as described above. The apparatus 900 comprises a measurement module 901 to measure or estimate the respiratory indicator and/or the physiological indicator. The measurement module 901 may be in communication with an interface 200 and any associated sensors attached to the interface 200, and/or an auxiliary unit or sensor(s) 905 which may be configured to provide signals indicative of the respiratory indicator and/or physiological indicator.

The apparatus 900 may also comprise a processor with optionally associated memory. The processor 903 may be connected to the components of the apparatus 900 to control the function of the various modules and components.

The apparatus 900 may also comprise clock/timer 902 to provide timing capabilities for the apparatus. Additionally, the apparatus 900 may include a display 904 for displaying information to a user for example any variables of the system, or information of interest.

In some embodiment the apparatus 900 may comprise or be associated with the respiratory therapy system 100 as described above. The apparatus 900 may comprise some or all of the components of the respiratory therapy system 100.

Features from one or more of the above methods may be combined with features of one or more other methods. Additionally, more than one method may be used together during a process of respiratory support of a patient.

The described systems can be useful for patients that are not spontaneously breathing, are sedated, or have reduced respiratory drive due to anaesthesia.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers are herein incorporated as if individually set forth.

The invention may also be said broadly to consist in the parts, elements and features referred to or indicated in the specification of the application, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Certain features, aspects and advantages of some configurations of the present disclosure have been described with reference to use of the gas humidification system with a respiratory therapy system. However, certain features, aspects and advantages of the use of the gas humidification system as described may be advantageously be used with other therapeutic or non-therapeutic systems requiring the humidification of gases. Certain features, aspects and advantages of the methods and apparatus of the present disclosure may be equally applied to usage with other systems.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

The invention claimed is:

1. A respiratory therapy system comprising:
one or more patient interfaces;
a processor configured to determine a duration of safe apnoea from a measured indicator; and
wherein the measured indicator or an indicator comprises measured carbon dioxide, and wherein the processor is configured to compare the measured carbon dioxide to a maximum carbon dioxide limit to determine the duration of safe apnoea.

2. The respiratory therapy system of claim 1, wherein the indicator is one or more of a respiratory indicator and/or a physiological indicator.

3. The respiratory therapy system of claim 1, wherein the indicator comprises, or is based on, carbon dioxide concentration, carbon dioxide clearance, respiratory rate, oxygen concentration, arterial oxygen, arterial carbon dioxide content, lung volume, lung compliance, lung/airway pressure, airway resistance/patency, V/Q mismatch (ventilation (V) — perfusion (Q)), heart rate, blood pressure, or metabolic rate.

4. The respiratory therapy system of claim 1, wherein the processor is configured to determine the duration of safe apnoea from a plurality of measured indicators comprising, or based on, two or more of carbon dioxide concentration, carbon dioxide clearance, respiratory rate, oxygen concentration, arterial oxygen, arterial carbon dioxide content, lung volume, lung compliance, lung/airway pressure, airway resistance/patency, V/Q mismatch (ventilation (V) — perfusion (Q)), heart rate, blood pressure, or metabolic rate.

5. The respiratory therapy system of claim 4, wherein the processor is configured to determine an average duration of safe apnoea from the plurality of measured indicators.

6. The respiratory therapy system of claim 4, wherein the processor is configured to determine a plurality of durations of safe apnoea from the plurality of measured indicators and further wherein the processor selects a shortest duration of safe apnoea from the plurality of durations of safe apnoea.

7. The respiratory therapy system of claim 1, wherein the processor is configured to compare or fit a model to the respiratory indicator to determine the duration of safe apnoea.

8. The respiratory therapy system of claim 1, wherein the respiratory therapy system is configured to measure carbon dioxide as the indicator or an indicator, wherein the carbon dioxide is measured based on expired carbon dioxide, transcutaneous carbon dioxide, or blood gases.

9. The respiratory therapy system of as claim 1, wherein the processor is configured to determine the maximum carbon dioxide limit from a look up table with different carbon dioxide limits.

10. The respiratory therapy system of as claim 9, wherein the look up table comprises different carbon dioxide limits depending on one or more or a combination of disease, age, height, weight, pregnancy status, and difficult airway type.

11. The respiratory therapy system of as claim 10, wherein the processor is configured to compare the measured carbon dioxide to a predetermined maximum carbon dioxide limit to predict the duration of safe apnea.

12. The respiratory therapy system of claim 1, wherein the one or more patient interfaces is a non-sealing cannula.

13. The respiratory therapy system of claim 1, wherein the measured carbon dioxide is calculated in real time.

14. The respiratory therapy system of claim 1, wherein an alert is generated based on the duration of safe apnoea.

15. A respiratory therapy system comprising:
a processor configured to determine a duration of safe apnoea from a measured indicator; and
wherein the measured indicator or an indicator comprises measured carbon dioxide, and wherein the processor is configured to compare the measured carbon dioxide to a maximum carbon dioxide limit to determine the duration of safe apnoea.

16. The respiratory therapy system of claim 15, wherein the indicator is one or more of a respiratory indicator and/or a physiological indicator.

17. The respiratory therapy system of claim 15, wherein the indicator comprises, or is based on, carbon dioxide concentration, carbon dioxide clearance, respiratory rate, oxygen concentration, arterial oxygen, arterial carbon dioxide content, lung volume, lung compliance, lung/airway pressure, airway resistance/patency, V/Q mismatch (ventilation (V) — perfusion (Q)), heart rate, blood pressure, or metabolic rate; or
wherein the processor is configured to determine the duration of safe apnoea from a plurality of measured indicators comprising, or based on, two or more of carbon dioxide concentration, carbon dioxide clearance, respiratory rate, oxygen concentration, arterial oxygen, arterial carbon dioxide content, lung volume, lung compliance, lung/airway pressure, airway resistance/patency, V/Q mismatch (ventilation (V) — perfusion (Q)), heart rate, blood pressure, or metabolic rate.

18. The respiratory therapy system of claim 17, wherein the processor is configured to determine an average duration of safe apnoea from the plurality of measured indicators; or wherein the processor is configured to determine a plurality of durations of safe apnoea from the plurality of measured indicators and further wherein the processor selects a shortest duration of safe apnoea from the plurality of durations of safe apnoea.

19. The respiratory therapy system of claim 15, wherein the processor is configured to compare or fit a model to the respiratory indicator to determine the duration of safe apnoea; or wherein the processor is configured to compare the measured carbon dioxide to a predetermined maximum carbon dioxide limit to predict the duration of safe apnoea.

20. The respiratory therapy system of claim 15, wherein the processor is configured to determine the maximum carbon dioxide limit from a look up table with different carbon dioxide limits; and wherein the look up table comprises different carbon dioxide limits depending on one or more or a combination of disease, age, height, weight, pregnancy status, and difficult airway type.

* * * * *

UNITED STATES PATENT AND TRADEMARK OFFICE
CERTIFICATE OF CORRECTION

| | |
|---|---|
| PATENT NO. | : 11,471,627 B2 |
| APPLICATION NO. | : 16/500329 |
| DATED | : October 18, 2022 |
| INVENTOR(S) | : Alicia Jerram Hunter Evans |

It is certified that error appears in the above-identified patent and that said Letters Patent is hereby corrected as shown below:

In the Specification

Column 10, Line 20, delete "helix" and insert -- heliox --.

In the Claims

Column 21, Line 62, Claim 9, delete "as claim" and insert -- claim --.

Column 22, Line 1, Claim 10, delete "as claim" and insert -- claim --.

Column 22, Line 5, Claim 10, delete "as claim" and insert -- claim --.

Signed and Sealed this
Fourteenth Day of March, 2023

Katherine Kelly Vidal
*Director of the United States Patent and Trademark Office*